United States Patent
Briggs

[11] Patent Number: 6,069,687
[45] Date of Patent: May 30, 2000

[54] CONTAMINANT DETECTOR

[75] Inventor: Dennis Briggs, Westchester, Pa.

[73] Assignee: Therakos, Inc., Exton, Pa.

[21] Appl. No.: 08/976,386

[22] Filed: Nov. 21, 1997

Related U.S. Application Data

[60] Provisional application No. 60/031,649, Nov. 22, 1996.

[51] Int. Cl.[7] ................................ G01N 33/48
[52] U.S. Cl. ........................... 356/39; 356/73
[58] Field of Search ...................... 356/39, 73, 410

[56] References Cited

U.S. PATENT DOCUMENTS

| | | |
|---|---|---|
| 4,324,556 | 4/1982 | Robertson et al. . |
| 4,407,295 | 10/1983 | Steuer et al. . |
| 4,775,794 | 10/1988 | Behmann . |
| 4,810,090 | 3/1989 | Boucher et al. . |
| 5,331,958 | 7/1994 | Oppenheimer . |
| 5,351,686 | 10/1994 | Steuer et al. ........................ 128/633 |
| 5,372,136 | 12/1994 | Steuer et al. . |
| 5,561,065 | 10/1996 | Schabron . |

FOREIGN PATENT DOCUMENTS

| | | |
|---|---|---|
| 0 268 025 | 5/1988 | European Pat. Off. . |
| 0 467 804 | 1/1992 | European Pat. Off. . |
| WO 94/29722 | 12/1994 | WIPO . |
| WO 95/04266 | 2/1995 | WIPO . |

OTHER PUBLICATIONS

"Silicon Carbide Blue LEDs", Product Brochure, Cree Research, Sep. 1994.
"VTB Process Diodes", Product information, date unknown.

*Primary Examiner*—Frank G. Font
*Assistant Examiner*—Roy M. Punnoose

[57] ABSTRACT

A contaminant detector including a light source for emitting light of a wavelength with peak emission corresponding to that of "blue" light or to that of light of even lower wavelength. Light is emitted through an arrangement containing a liquid sample having a given contaminant, and a sensing arrangement on the other side of the liquid sample detects the amount of light passing through the liquid sample. The measured light is converted into a value indicative of the relative presence of the given contaminant in the liquid sample. It is contemplated that other types of light can be used, particularly if the color of the light is matched, or even approximately matched, with that portion of the liquid sample that is not to be measured (i.e. the "background" or "non-contaminant" portion of the liquid.

27 Claims, 8 Drawing Sheets

CONTAMINANT DETECTOR

This case claims benefit of Provisional application Ser. No. 60/031,649 filed Nov. 22, 1996.

FIELD OF THE INVENTION

The present invention generally relates to apparatus for quantitatively determining the presence of a given contaminant or contaminants in a given liquid. The present invention also generally relates to apparatus for measuring hematocrit in human blood, or in blood products extracted or derived from human blood, and to processes for undertaking such measurements.

BACKGROUND OF THE INVENTION

Historically, it has often been important to determine the amount of a given contaminant or foreign substance present in a given product. For example, determinations of this nature can be vitally important if a product, during manufacture, needs to be screened in order that unduly contaminated portions thereof can be safely rejected and prevented from reaching the consumer public. Some examples of products in which such determinations might be important are, but are not limited to, the following: clear solvents (such as alcohol, paint thinner, turpentine, etc.); liquid pharmaceutical or medicinal products (e.g. liquid cold/fever medicines, hydrogen peroxide, liquids for use in vaporizers); various clear or "dye-free" products in the market place (including, among others, liquid soaps, detergents and waxes, shampoos, hair sprays, cosmetics, deodorants, topical medications, beverages, ingestible and parenteral alimentation solutions); fossil fuels, such as petroleum (either in crude or refined form); and other liquids which may either be essentially clear in nature or may have a given base color.

As another example, in the context of medicine and physiology, there has often been a need to accurately determine the levels of certain substances, which may be considered "contaminants", in a given portion of a patient's bodily fluids. Such substances may be foreign to or naturally occurring in the human body. They may be innately undesirable or physiologically beneficial. By way of example, a brief discussion of red blood cells as a possible "contaminant" in certain contexts is provided herebelow.

Normally, human blood will contain a quantity of red blood cells and a quantity of white blood cells, in addition to other components. Historically, it has often been important to measure, with some accuracy, the presence of these constituent portions in a patient's blood, in order to assist, for example, in the diagnosis of given diseases or disorders.

One convenient parameter for assessing the relative presence of different constituents in a sample of patient's blood is the hematocrit parameter. Nominally, the hematocrit parameter will indicate, with some degree of accuracy, the degree to which the volume of the patient's blood is accounted for by red blood cells. Generally, the hematocrit value can be expressed as a percentage or a decimal proportion, or by any other means for clearly expressing such a ratio or proportion. Thus, the hematocrit of a blood sample or blood product sample can be considered, for most purposes, as being roughly equivalent to the percentage (by volume) of the blood or blood product sample that is constituted by red blood cells.

Conventionally, hematocrit measurements have often been determined for whole-blood samples, i.e. blood samples withdrawn directly from a patient which are not subject to subsequent separation, treatment or other modification. In addition, however, a tremendous value has often been placed on measuring hematocrit values with regard to a blood sample that has itself already undergone some type of modification or alteration, such as blood products, having been selectively extracted from a whole blood sample, that contain, for instance, a preponderance of white blood cells. In such instances, it is often extremely vital to ensure that hematocrit levels will not be excessively high, or, more particularly, that they will not exceed a predetermined threshold. It is in such instances that, for practical purposes, the red blood cells may be viewed as a "contaminant".

In the context of blood products containing a preponderance of white blood cells, the need for accuracy in hematocrit measurements has been widely recognized. Particularly, it has been widely recognized that the acceptable margin of error in taking hematocrit measurements of blood products containing a preponderance of white blood cells is tremendously smaller than in the case of measuring whole-blood samples. Therefore, even though a margin of error built into a given measuring apparatus or process might arguably have a negligible effect in the context of whole blood samples (e.g., blood samples in which the hematocrit value is on the order of magnitude of 50% or higher), it would, in proportion to the actual hematocrit values present, be much more significant in the context of a blood sample containing a preponderance of white blood cells (e.g., a blood sample having a hematocrit value on the order of magnitude of only a few percent or less).

The need for a high degree of accuracy at low levels of hematocrit might be especially important in order to properly diagnose or verify a particular disorder or disease the patient might have in order to provide proper treatment for the patient. For example, if a blood sample is extracted from a patient, and then is subsequently separated in a centrifuge or other cell separating device, it might be extremely important to ensure that the hematocrit level is sufficiently low in order for the blood sample to be able to undergo subsequent treatment, such as irradiation in an irradiation apparatus. In this vein, it is a distinct possibility that an unduly high level of hematocrit in a patient's blood sample (i.e., a blood sample containing a preponderance of white blood cells), even on the order of magnitude of a few tenths of a percentage point or less, could subsequently result in relatively ineffective treatment (thus either delaying or even jeopardizing the possibility of the patient's recovery), or could simply represent an undesirable waste of time and resources (in that a complete restart of the procedures of withdrawing, centrifuging and treatment might be necessary).

Conventionally, one method of measuring hematocrit involves the centrifuging of a sample with a standard centrifuge and a capillary tube. A physical measurement is made of packed red cells in the tube, and a hematocrit calculation is derived therefrom. However, disadvantages are found in that the blood must first be collected and then centrifuged, and in that results are generally not immediately available. Further, results tend not to be highly accurate at lower hematocrit levels, such as hematocrit levels of about 30% or less.

Another conventional method contemplates a technique in which two LED (light-emitting diode) emitters of differing wavelength (typically red [i.e., generally about 600 nm] and green [i.e., generally about 500 nm]) are modulated through a sampling cuvette. A photodiode and electrical circuit amplify the light that has originated from the emitter and passed through the cuvette. Once the LED has been switched on and permitted to stabilize, a measurement is made of the difference in the signal amplitude of the modulated light. A computer calculates the hematocrit measurement based differences in the light reaching the detector. Results obtained in connection with such systems tend not to be accurate with respect to blood products samples having significantly low hematocrit levels (such as about 6% or less), and response time tends to be slow in view of the use of modulated light and in view of the response time of the photodiode circuit. These systems tend to be highly complex in view of the light modulation technique and the need to compute the difference between two detector readings.

U.S. Pat. No. 5,351,686 to Steuer et al. discloses an arrangement in which a disposable cuvette, through which pulsatile flowing blood is to pass, has a conduit with two opposed walls having a predetermined separation therebetween that varies with each pulse of the flowing blood. In this procedure, it is possible to produce a value indicative of the change in a patient's hematocrit from one point in time to another, as well as values indicating absolute hematocrit. However, since this patent to Steuer et al. appears only to contemplate the detection of hematocrit in whole blood, it would appear that the apparatus disclosed therein may not be as accurate as desired at relatively low levels of hematocrit (as discussed more generally heretofore).

U.S. Pat. No. 5,372,136 to Steuer et al. discloses a system and method for hematocrit monitoring in which, for example, a finger may be inserted into a tube-like structure or a clip may be placed on an earlobe. In either case, a photodiode arrangement assists in the determination of a hematocrit value on the basis of the extinction of various wavelengths of light that have traveled through the human body part in question. This procedure involves what may be called a "non-invasive" detection of hematocrit. However, it only appears to be capable of determining a value indicative of a change in a patient's hematocrit from one point in time to another, and not absolute values of hematocrit. Further, the apparatus disclosed in this patent to Steuer et al. would also appear to encompass similar disadvantages as described immediately above and more generally heretofore (that is, it may not be as accurate as desired at low levels of hematocrit). Additionally, there would also appear to be a potential distorting factor arising from the passage of light through additional, intervening media, e.g., the patient's skin, bone, muscle and other bodily components.

It is believed that the known devices and processes discussed and alluded to hereinabove, for the most part, are complex and expensive, and present results that are not as accurate as may be desired.

In view of the foregoing, a need has arisen for the provision of a detector or detectors that can, in the presence of a given liquid containing an undesirable substance or contaminant therewithin, accurately ascertain the degree of the contaminant's presence.

SUMMARY OF THE INVENTION

In accordance with at least one embodiment of the present invention, an apparatus and method are contemplated in which preferably a single light source, for emitting light of a wavelength with peak emission generally corresponding to that of "blue" light in the visible spectrum or to that of light of even lower wavelength, emits light through an arrangement containing a liquid sample, for which it is desired to measure or detect a given contaminant. Further, a sensing arrangement located on the other side of the liquid sample preferably detects the amount of light passing through the liquid sample. Appropriate circuitry will preferably convert the measured light into a value indicative of the relative presence of the given contaminant in the liquid sample. With such an arrangement, it is also conceivable to detect instantaneous changes in the level of the contaminant in question.

In this posture, it has been found that significantly accurate measurements of the presence of a given contaminant in a given liquid can be obtained if, as a general rule, a principle of "color affinity" is followed in exposing tne liquid to light during a detection procedure. For example, since "blue" wavelengths of light (or light of lesser wavelengths) tend to mimic the "color", or lack of color, present in white blood cells more closely than does light of higher wavelengths (such as red and/or green wavelengths), it appears that, especially in the context of a blood sample containing a preponderance of white blood cells, the presence of red blood cells is much more likely be distinguished by a detector using blue light (or light of lesser wavelengths) than if red or green light were being passed through the blood sample in question. It will be appreciated that, consistent with the present invention, similar principles can be applied to measuring contaminants in liquids other than bodily fluids including, without limitation, consumer and industrial products.

Thus, a great deal of accuracy can be obtained by essentially matching, or even approximately matching, the color of the light being emitted to that portion of the liquid sample that is not being directly measured (i.e., the non-contaminant, "background" or "fundamental" portion of the liquid) but whose purity may be derived through measurement of the contaminant content therein. In this manner, it would appear to be much easier to ascertain the presence of contaminants that differ significantly in color from the light being directed through the liquid sample in question.

In accordance with at least one preferred embodiment of the present invention, a particular advantage may be found, in the context of measuring hematocrit in a blood product sample containing a preponderance of white blood cells, and especially in instances in which the blood produce sample is destined for irradiation in an irradiation apparatus, in that light having a wavelength substantially corresponding to that of "blue" light can be considered as closely mimicking UV-A light (i.e., light having a wavelength of about 352 nm), which UV-A light itself is often used in such irradiation procedures. Thus, by closely mimicking the physical characteristics of light that is later to be used on the same blood product sample during an irradiation procedure, the likelihood that any portion of the blood product sample being measured in a hematocrit detector will be unduly effected or altered by the light from the LED is greatly reduced.

In summary, one aspect of the present invention broadly contemplates a device for measuring hematocrit, the device including:

a light source for emitting light along a predetermined path;

an arrangement for disposing a portion of a human blood sample in the path of light emitted by the light source, wherein the light source emits light having a peak emission wavelength no greater than that of blue light;

an arrangement for sensing light that has originated from the light source and that has passed through a portion of a human blood sample disposed, by the disposing arrangement, in the path of light emitted by the light source; and an arrangement for converting the light sensed by the sensing arrangement to a hematocrit value.

In another aspect, the present invention broadly contemplates apparatus for measuring a contaminant present in a liquid, the apparatus comprising:

a light source for emitting light along a predetermined path;

an arrangement for temporarily disposing a portion of a liquid sample, the sample containing a contaminant portion and a non-contaminant portion, in the path of light emitted by the light source, the contaminant portion of the liquid being identifiable by emission thereof of light predominantly comprised of a first wavelength and the non-contaminant portion of the liquid being identifiable by emission thereof of light predominantly comprised of a second wavelength different from the first wavelength;

an arrangement for sensing light that has originated from the light source and that has passed through a portion of a liquid sample disposed, by the disposing arrangement, in the path of light emitted by the light source; and an arrangement for converting the light sensed by the sensing arrangement to a value indicative of the presence of the contaminant portion in the liquid sample;

wherein the light source comprises an arrangement for emitting light having a peak emission wavelength that is substantially no greater than the second wavelength.

In yet another aspect, the present invention broadly contemplates a method of measuring a contaminant present in a liquid, the method including the steps of:

providing a light source for emitting light along a predetermined path;

obtaining a liquid sample containing a contaminant portion and a non-contaminant portion, the contaminant portion of the liquid being identifiable thereof by emission of light predominantly comprised of a first wavelength and the non-contaminant portion of the liquid being identifiable by emission thereof of light predominantly comprised of a second wavelength different from the first wavelength, the non-contaminant portion having a given color;

disposing a portion of the liquid sample in the path of light emitted by the light source;

emitting light through the liquid sample portion;

sensing light that has originated from the light source and has passed through the liquid sample portion; and converting the light sensed to a value indicative of the relative presence of one of:

the contaminant portion in the liquid sample; and the non-contaminant portion in the liquid sample;

wherein the light source emits light having a peak emission wavelength that is substantially no greater than the second wavelength.

BRIEF DESCRIPTION OF THE DRAWINGS

The present invention, as contemplated in accordance with at least one preferred embodiment thereof, will be more readily understood with reference to the accompanying drawings, wherein.

DESCRIPTION OF THE PREFERRED EMBODIMENTS

Figure 1:
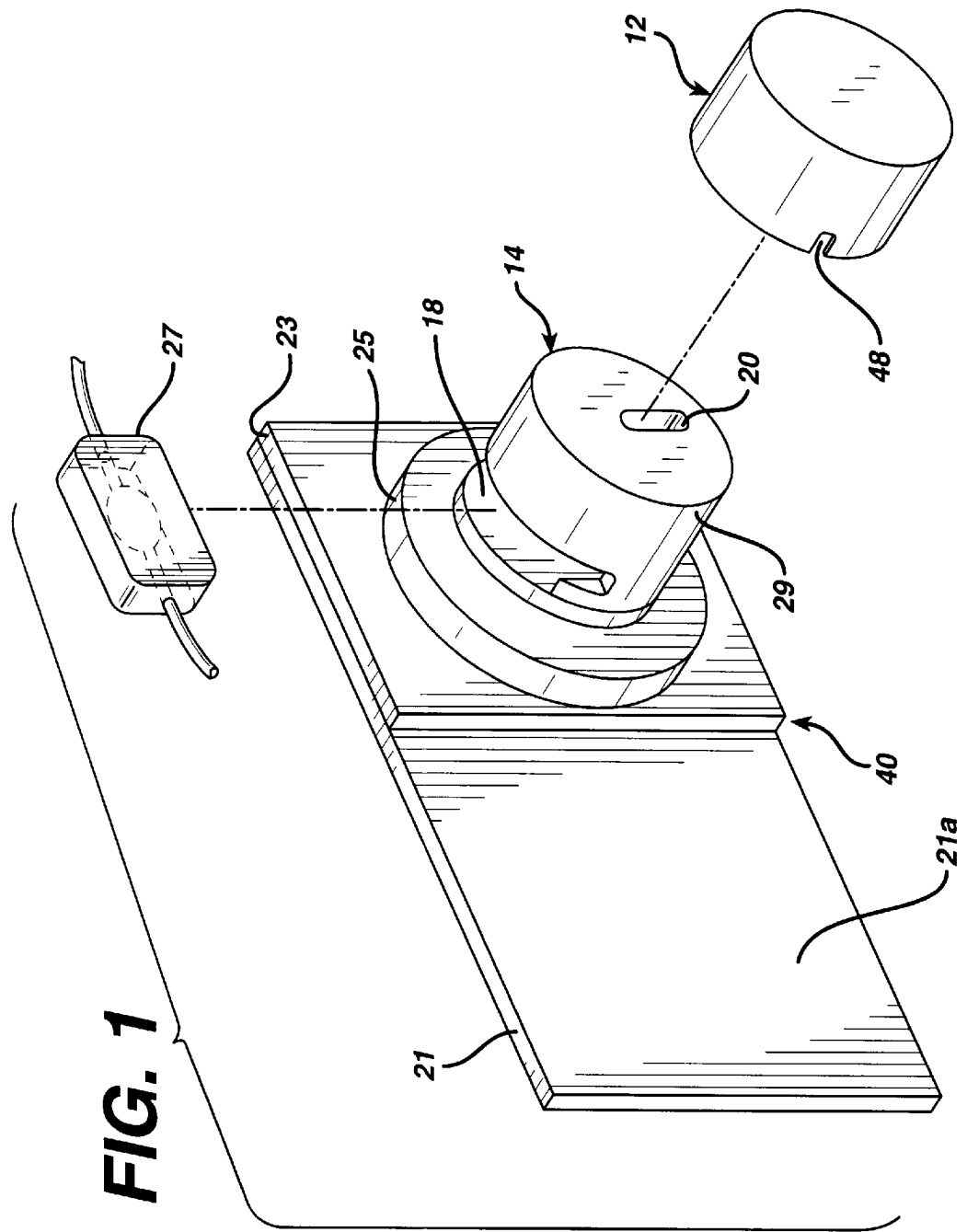
FIG. 1 illustrates a contaminant detector in exploded view.

FIG. 1 illustrates a contaminant detector according to a preferred embodiment of the present invention. Particularly, FIG. 1 shows a contaminant detector 10, in exploded view, as having cover 12 and a main body 14. Also shown is a cuvette 27 that is selectively insertable into the main body 14 in a manner that will be described in greater detail hereinafter.

In accordance with at least one preferred embodiment of the present invention, a mounting block 23 may be mounted on a suitable mounting plate 21. In turn, mounting block 23 may preferably form a base for main body 14. As shown in FIG. 1, main body 14 could preferably be constituted by a larger cylindrical portion 25 and a smaller cylindrical portion 29 (i.e., "larger" and "smaller" in terms of their relative diameters). Further, on a surface 21a of mounting plate 21, it is conceivable to mount, in any appropriate manner, circuitry for the purpose of processing measurements taken by the detector 10. Alternatively, such circuitry could be provided on that surface of mounting plate 21 disposed opposite from surface 21a.

Preferably, smaller cylindrical portion 29 will have a slot 18 disposed therein that is suitable for accommodating the aforementioned cuvette 27. Also preferably provided in cylindrical portion 29 is a light-emitting diode (LED) arrangement or other suitable light source 20 for emitting light during measurement procedures.

Figure 5:
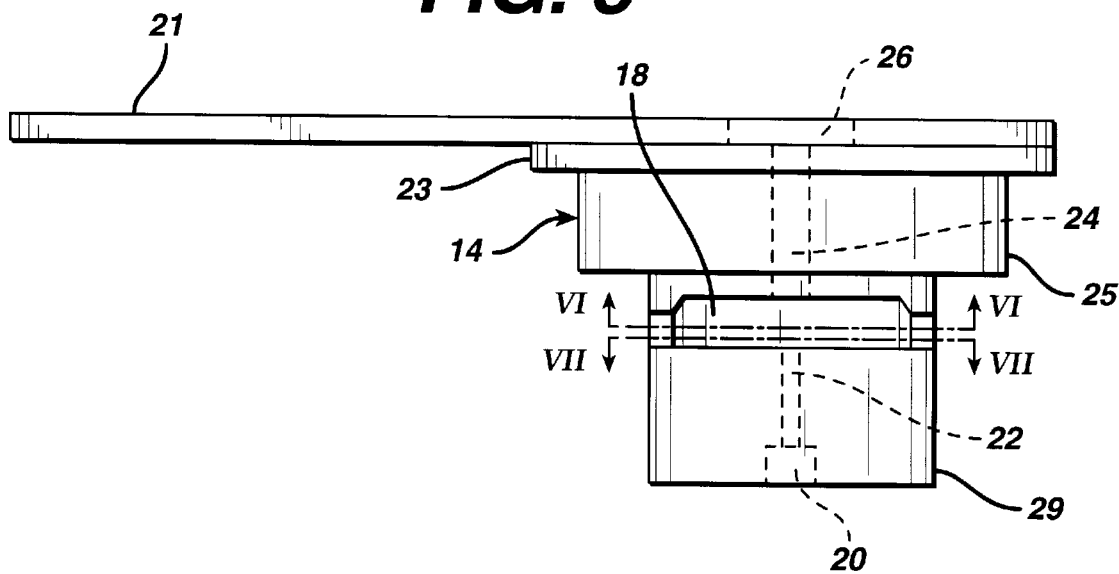
FIG. 5 is a plan view of the contaminant detector shown in FIGS. 1, 3 and 4.

To facilitate the propagation of light through cuvette 27 (when inserted in main body 14), the main body further preferably comprises a first passage 22 leading from LED 20 to slot 18 and a second passage 24 leading from the slot 18 to a suitable sensing arrangement 26 (see FIG. 5).

Preferably, slot 18 will accommodate cuvette 27 in a manner that permits the light emitted by LED 20 to pass through cuvette 27 and onward to sensing arrangement 26 (again, see FIG. 5). Preferably, for the duration of a detection procedure, cover 12 will be placed over main body 14 in such a manner as to significantly minimize, if not virtually completely eliminate, the ingress of ambient light (i.e., light from outside of the apparatus) towards cuvette 27.

Figure 2:
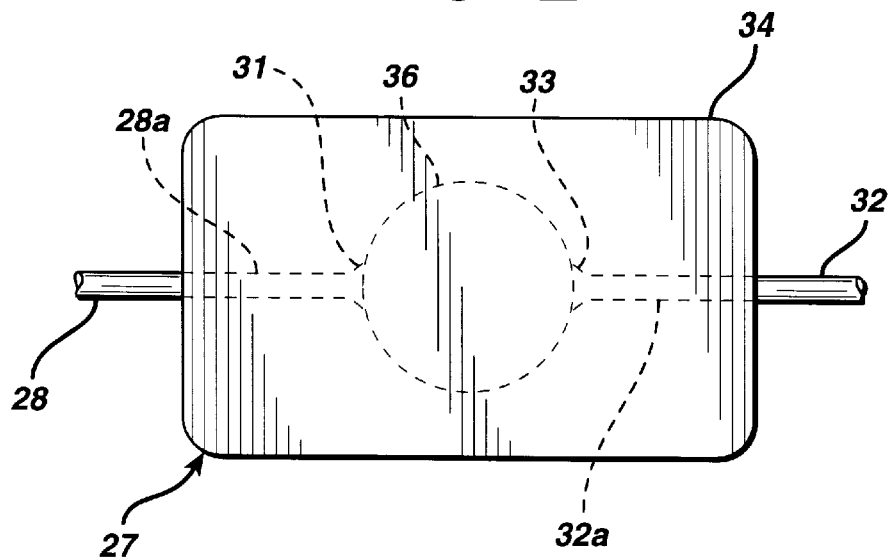
FIG. 2 provides a detailed illustration of a cuvette.

FIG. 2 more closely illustrates a cuvette 27 that may be utilized in accordance with a preferred embodiment of the present invention. Preferably, cuvette 27 will include an infeed line 28, an outfeed line 32 and a main body portion 34.

Main body portion 34 will preferably be so configured as to include therewithin a portion defining a "flattening"

chamber (which could be alternatively termed an "exposure", "detection" or "testing" chamber) 36 of significantly small thickness to effectuate the provision of a significantly thin layer of a blood product sample in the path of light emitted from the light source 20. In one embodiment of the present invention, the thickness of chamber 36 could be about 0.030 inch (resulting in a blood film layer of similar thickness), but slightly larger or smaller thicknesses could also be used.

Preferably, main body portion 34 will also be so configured as to readily accommodate infeed and outfeed lines 28 and 32 so that infeed and outfeed lines 28 and 32 may respectively direct blood portions into and out of chamber 36 via suitable interior conduits 28a and 32a. Interior conduits 28a and 32a may be generally tubular in nature and may effect a transition into chamber 36 via suitably configured transition zones 31 and 33. Preferably, chamber 36 will be so configured as to present a thin, and substantially laminar, layer of liquid to light emitted from LED arrangement, or other suitable light source 20 (see FIG. 1). In accordance with at least one preferred embodiment of the present invention, at least chamber 36 is made of an essentially transparent material (e.g., a clear plastic). It will be understood that the balance of the main body portion 34, as well as the infeed and outfeed lines 32, 34 may be made of similar material (although materials of greater opacity may be more preferable for these components in order to further inhibit the ingress of ambient light into chamber 36).

Figure 3:
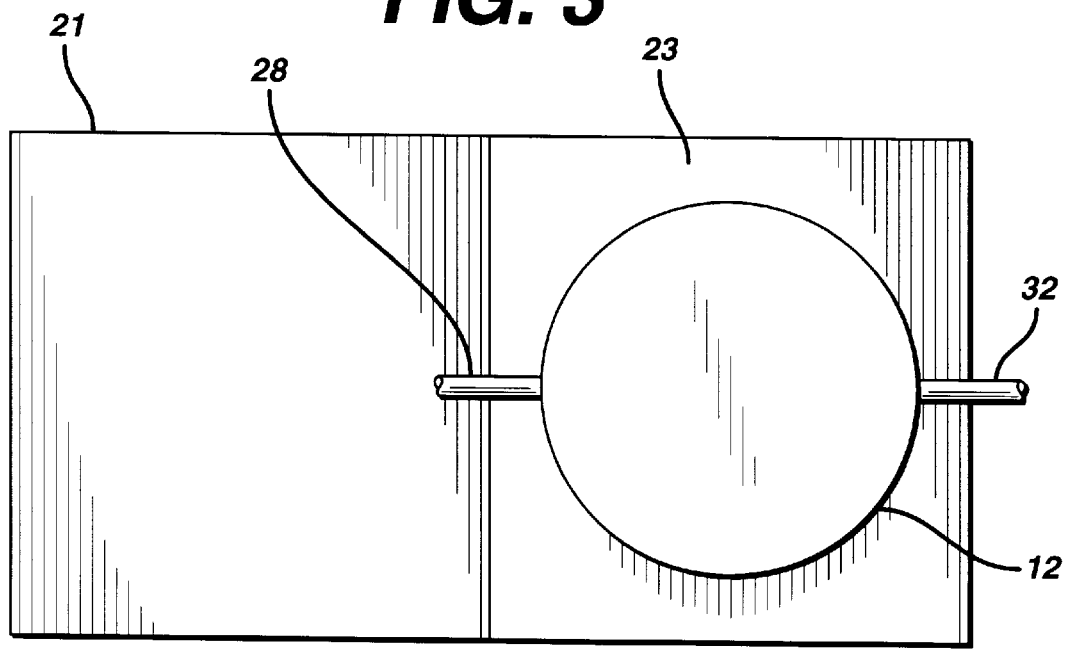
FIG. 3 is a front elevational view of the contaminant detector illustrated in FIG. 1, with a cover and cuvette in place (in preparation for a detection procedure)

FIG. 3 illustrates the contaminant detector with the cuvette 27 inserted into slot 18 (see FIG. 1) and with cover 12 in place, in preparation for a detection procedure.

Figure 4:
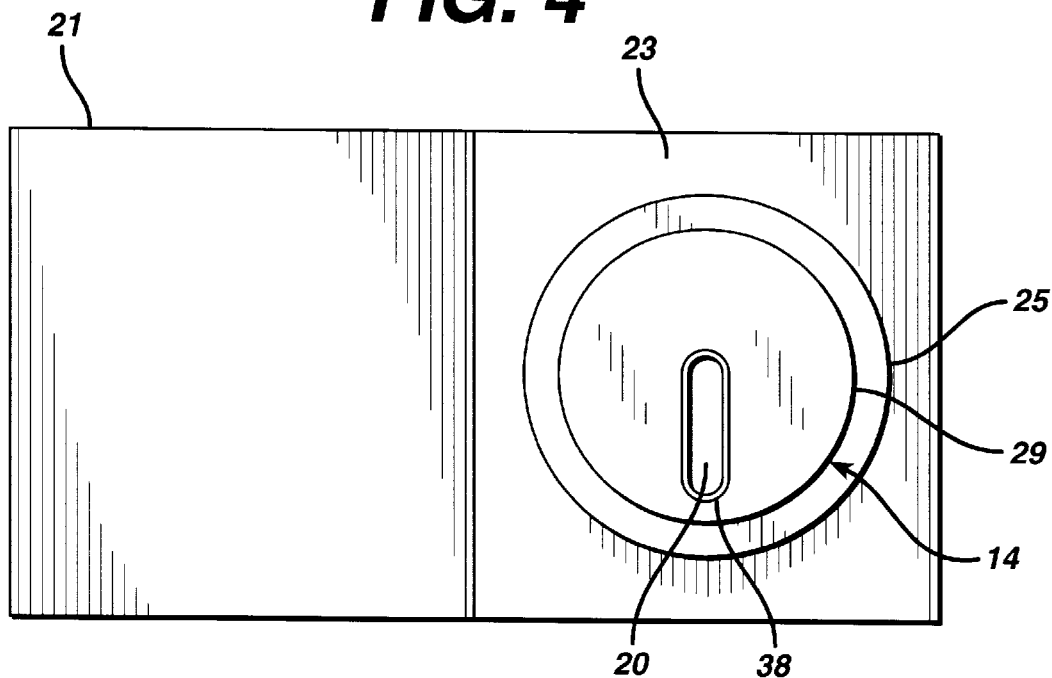
FIG. 4 is substantially the same view as FIG. 3, but with the cuvette and cover being removed.

FIG. 4 is a front elevational view of a contaminant detector according to the present invention, with the aforementioned cover 12 being removed. The aforementioned LED arrangement 20 is preferably positioned in a suitably dimensioned slot 38.

FIG. 5 is a plan view of the contaminant detector shown in FIG. 3. As illustrated, slot 18 preferably spans at least the diameter of the smaller cylindrical portion 29 of main body 14.

Figure 6:
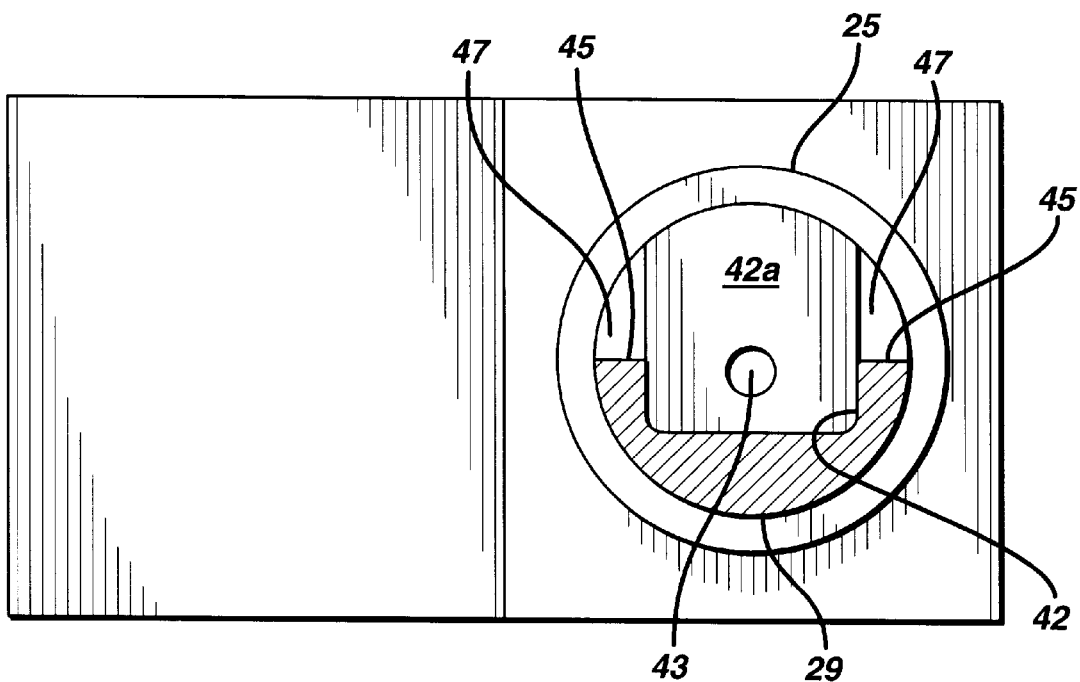
FIG. 6 is a cutaway view taken substantially along the line VI—VI shown in FIG. 5.

FIG. 6 is a cut-away view taken substantially along the line VI—VI shown in FIG. 5. As shown, slot 18 will preferably be so configured as to fully accommodate cuvette 27, and thus preferably includes a downward recessed portion 42. Preferably, downward recessed portion 42 will contain a window 43 that, upon placement of cuvette 27 in slot 38, will be aligned with the aforementioned flattening chamber 36 of cuvette 27 so as to direct light into second passage 24 (see FIG. 5).

Figure 7:
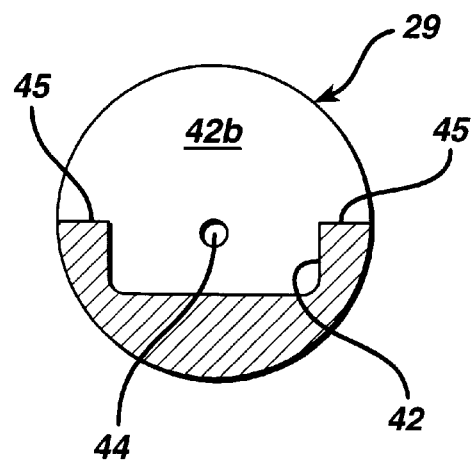
FIG. 7 is a cutaway view taken substantially along the line VII—VII shown in FIG. 5.

FIG. 7 is a cut-away view substantially taken along the line VII—VII shown in FIG. 5. As shown, this portion of main body 14 will preferably have a hole 44 disposed therewithin configured for directing LED or other light from first passage 22 (see FIG. 5) towards flattening chamber 36 of cuvette 27 and thence to the aforementioned window 43.

FIGS. 6 and 7 illustrate that, in accordance with at least one preferred embodiment to the present invention, the aforementioned cuvette-accommodating slot 18 (see FIG. 5) can preferably be constituted by: downward recessed portion 42, substantially horizontal ledge portions 45 and substantially vertical wall portions 47. Downward recessed portion 42 itself may preferably be constituted by a first vertical wall portion 42a (as shown in FIG. 6) and a second vertical wall portion 42b (as shown in FIG. 7).

Preferably, portions 42a, 42b, 47 and 45 will be so dimensioned and configured as to adequately accommodate cuvette 27 when the same is inserted into slot 18 and supported within downward recessed portion 42. In this regard, when cuvette 27 (see FIG. 2) is inserted into downward recessed portion 42, a significant portion of main body 34 of cuvette 27 will preferably be cradled in downward recessed portion 42. So configured, the infeed and outfeed lines 28 and 32 will preferably respectively rest on corresponding horizontal ledge portions 45, whereas opposite longitudinal ends of cuvette 27 will substantially abut against corresponding vertical wall portions 47. Preferably, with respect to the view shown in FIG. 6, vertical wall portion 42a will preferably be axially more recessed than vertical wall portions 47, in order to readily accommodate the thickness of main body 34 beyond the infeed and outfeed lines 28 and 32. With infeed line 28 and outfeed line 32 of cuvette 27 resting on horizontal ledge portions 45, the same will also preferably be accommodated by suitably dimensioned recesses 48 in cover 12 (one of which is shown in FIG. 1).

Figure 8:
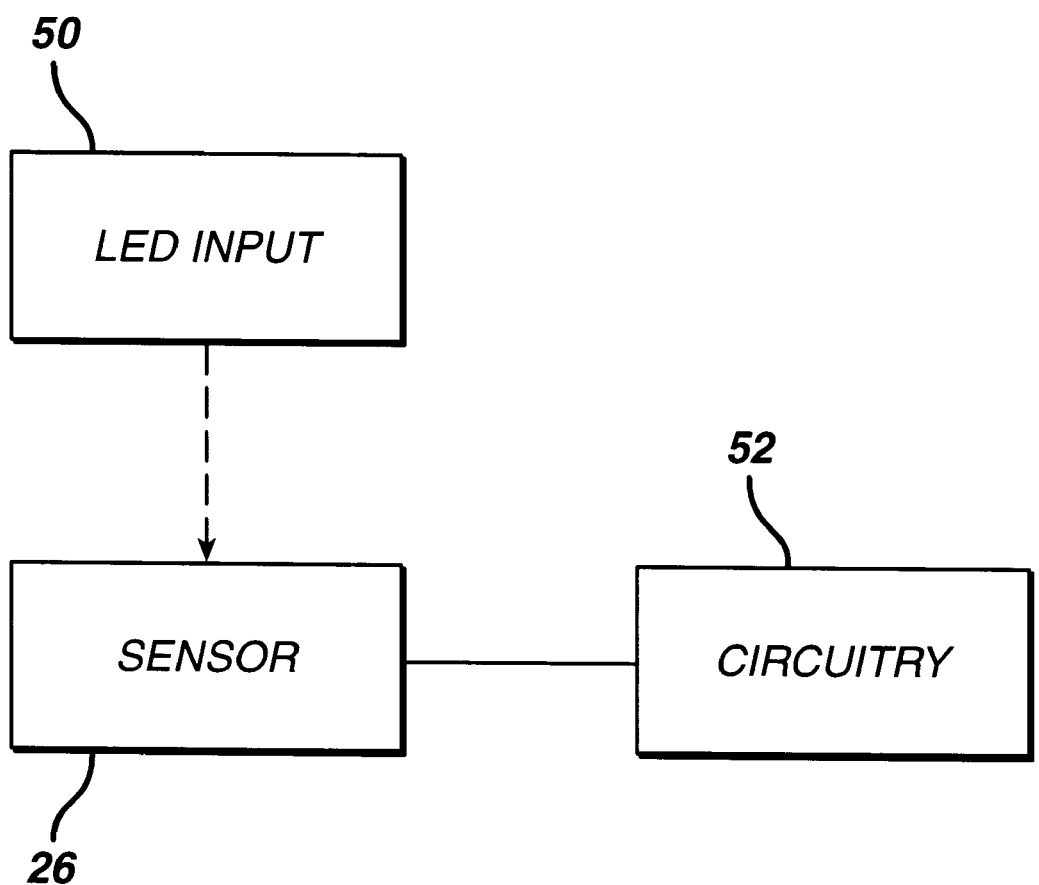
FIG. 8 is a schematic illustration of a detection arrangement.

Preferably, window 43 leads to passage 24 and terminates at suitable sensing device, or sensor, 26 (see FIG. 5). Such a sensor 26 is schematically indicated in FIG. 8, with the LED input being indicated schematically at 50. Preferably, sensor 26 will be connected to suitable circuitry and/or programming 52 for the purpose of determining the actual contaminant level in the liquid sample in question.

Figure 9:
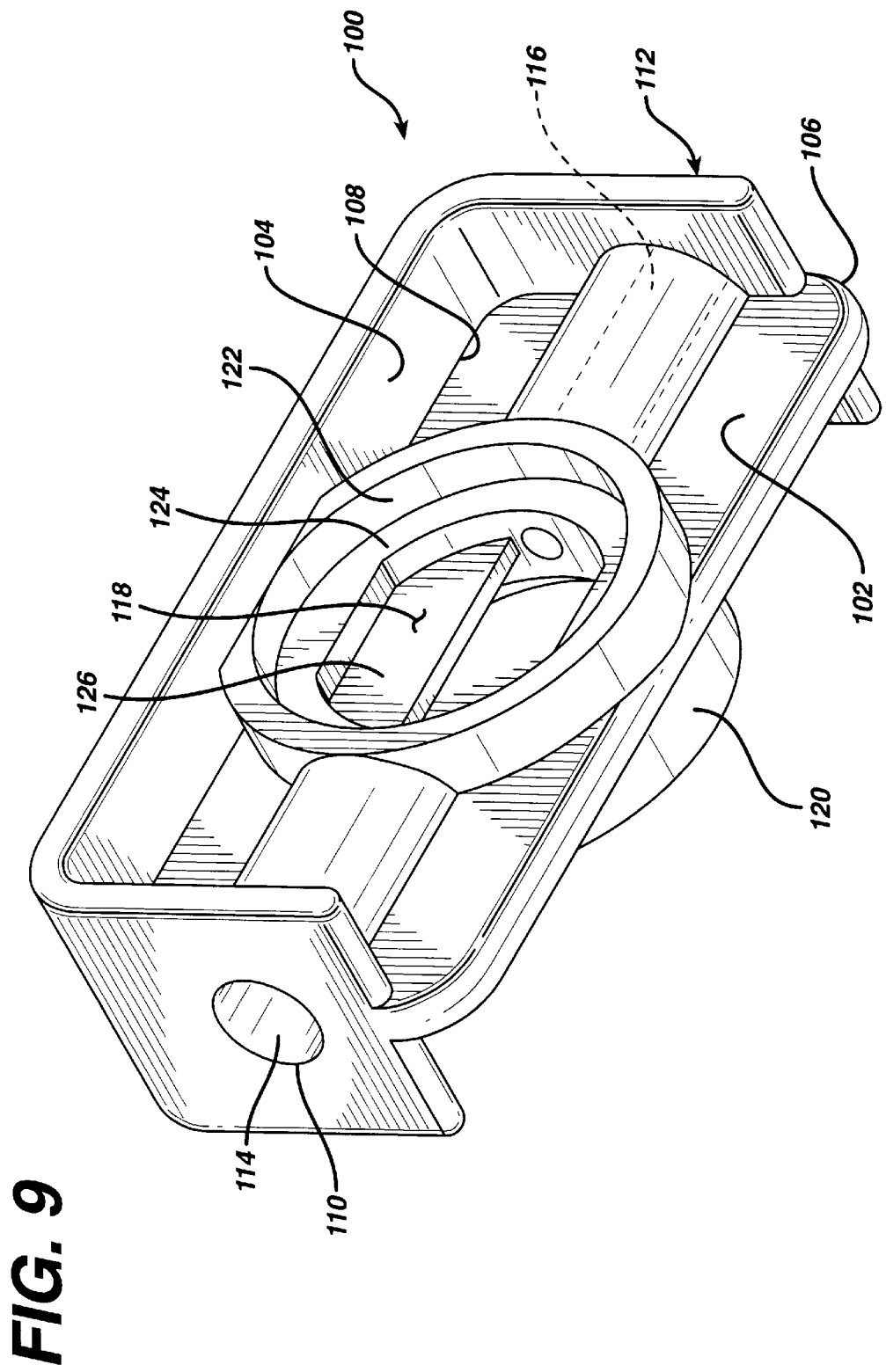
FIG. 9 is a perspective view of an alternative cuvette according to the present invention.
Figure 10:
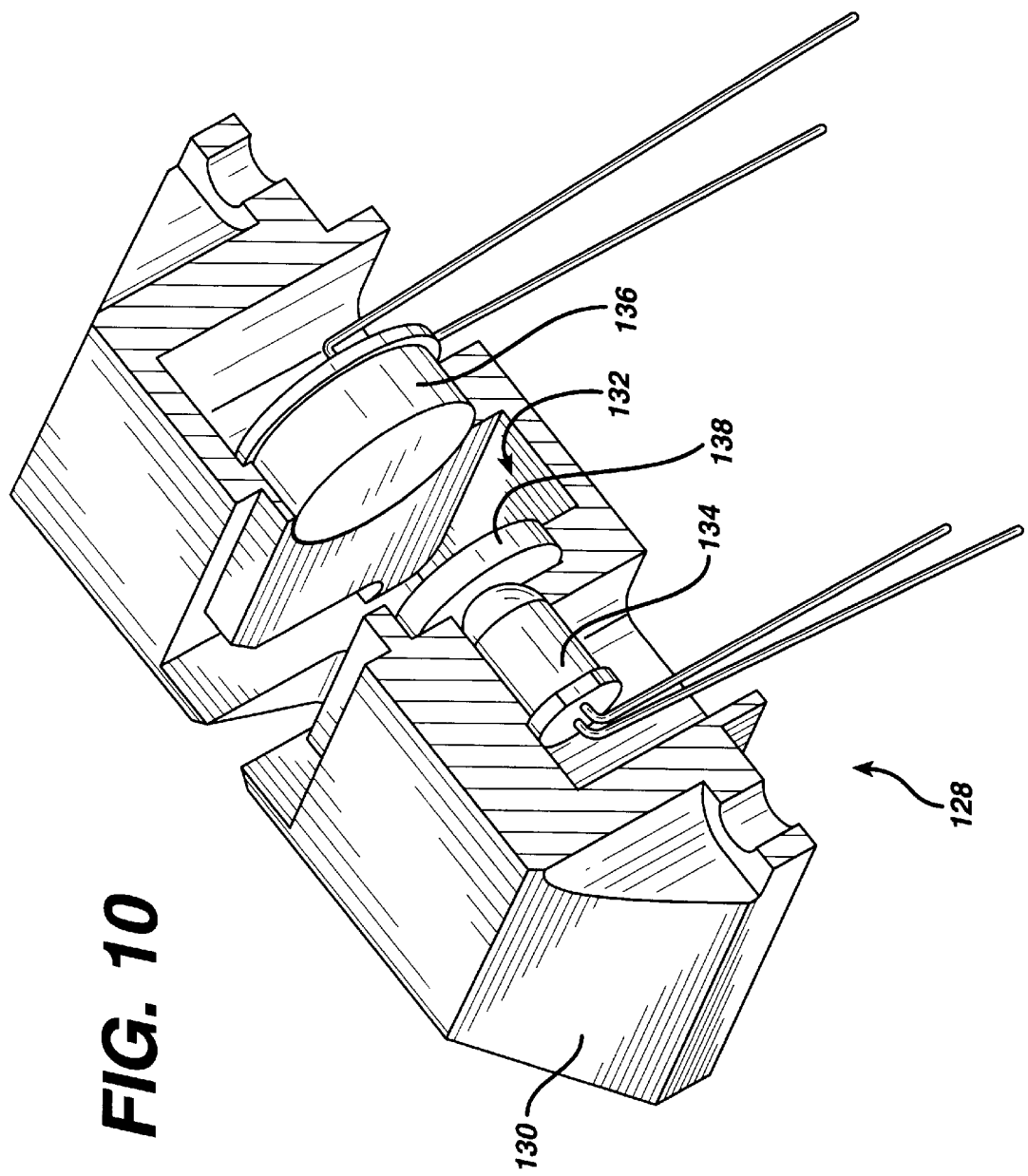
FIG. 10 is a perspective view, in partial section, of an alternative light assembly according to the invention for receiving the cuvette of FIG. 9.
Figure 11:
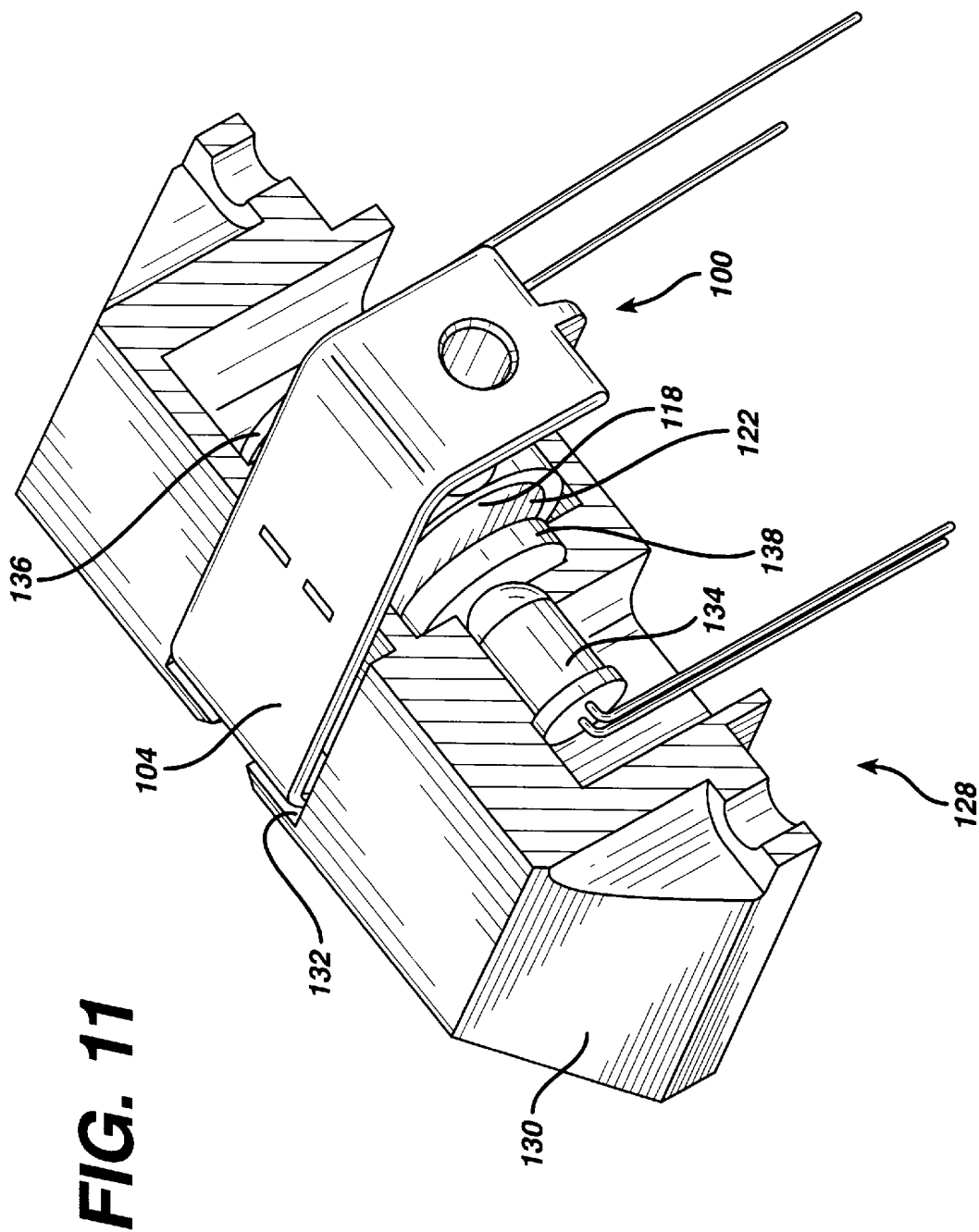
FIG. 11 is a perspective view of the cuvette of FIG. 9 received within a recess on the light assembly of FIG. 10.

FIGS. 9 to 11 illustrate a further embodiment of the invention. FIG. 9 shows an alternative cuvette 100 molded of an opaque plastic or other suitable material. The cuvette 100 comprises a flat elongated body 102 having an integral light shield flange 104 molded over ends 106 and an upper edge 108 of the body 102. Ports 110 and 112 connect to the tubing (not shown) as in the prior embodiment. Passageways 114 and 116 lead from ports 110 and 112 respectively into a discoidal viewing chamber 118. The chamber 118 is defined by an annular wall 120 normal to and penetrating the body 102. A pair of transparent windows 122 are sonically welded within the wall 120, abutting an annular ledge 124 within the chamber 118, to enclose the chamber 118. A longitudinal vane 126, coplanar with the body 102, extends through an upper portion of the chamber 118 between the windows 122 to promote laminar flow of sufficient velocity to carry any entrained air bubbles out of the chamber 118.

FIG. 10 shows an optical assembly 128 for receiving the cuvette 100 (not shown in FIG. 10). The assembly 128 comprises a body 130 formed of an opaque material having a recess 132 shaped to receive the cuvette 100, with an LED 134 on one side thereof and a photodiode 136 on an opposite side thereof. A window 138 separates the LED 134 from the recess 132. FIG. 11 shows the cuvette 100 received within the recess 132. The light shielding flange 104 and the optical assembly body 130 shield the chamber 118 from ambient light sources. The LED 134 can direct its light through its window 138, through the chamber windows 118, and the chamber 118 to be received by the photodiode 136. The hematocrit level of fluids flowing through the chamber 118 can thus be measured quickly and easily.

It is to be understood that, in accordance with at least one preferred embodiment of the present invention, the contaminant detectors described and illustrated with respect to FIGS. 1 to 11 provide only illustrative examples and are in no way meant to limit the scope of the present invention.

It will be appreciated that the structural and functional aspects of the present invention may be applicable to a wide variety of contexts, involving a wide variety of liquids and associated contaminants. Thus, although specific reference has been made to the context of detecting the presence of red blood cells in a human blood sample containing a preponderance of white blood cells, it is to be understood that other liquids and other contaminants can conceivably be adopted within the scope and spirit of the present invention, especially by employing the concept of "color affinity" described and alluded to throughout the instant application. Examples of such liquids include, but are not limited to: clear solvents (such as alcohol, paint thinner, turpentine, etc.); liquid pharmaceutical or medicinal products (e.g. liquid cold/fever medicines, hydrogen peroxide, liquids for use in vaporizers); various clear or "dye-free" consumer products in the market place (including, among others, liquid soaps, detergents and waxes, shampoos, hair sprays, cosmetics, deodorants, topical medications, beverages, parenteral alimentation solutions); fossil fuels, such as petroleum (either in crude or refined form); and other liquids which may either be essentially clear in nature or may have a given base color.

It will be appreciated that, in accordance with at least one preferred embodiment of the present invention, and especially in the context of determining hematocrit values in human blood or blood product samples (particularly blood samples containing a preponderance of white blood cells), it is desirable to utilize light that has no greater a wavelength than that associated with "blue" light. In at least one embodiment of the present invention, this may translate to about 466 nm or less. To date, light having a wavelength of as low as 430 nm has been used, and it is conceivable to utilize light of even lower wavelength. As discussed heretofore, it would appear that such wavelengths (i.e., those associated with "blue" light or less, such as about 466 nm or less) provide several advantages including, but not necessarily limited to: the likelihood that the presence of red blood cells would be distinguished more easily against the background of white blood cells; and the compatibility of such light with the type of light that may be used in an irradiation procedure such as UV-A light (i.e., light having a wavelength of about 352 nm) with the resultant likelihood that the blood product sample being measured will not be unduly affected or altered by the light from the LED.

In accordance with at least one embodiment of the present invention, it has been found that blue LED's manufactured by Cree Research, Inc. of Durham, N.C., are particularly effective, particularly, the "C470 Series Silicon Carbide Blue LED's."

In accordance with at least one embodiment of the present invention, a suitable photodiode may preferably be used as the sensing arrangement 26 illustrated and described herein. The "VTB Process Photodiodes" manufactured by EG&G VACTEC of St. Louis, Mo., have been found to be particularly effective.

Preferably, in accordance with at least one embodiment of the present invention, essentially any suitable type of circuitry may be used for the purpose of converting the light measured by the aforementioned sensing arrangement (such as a photodiode) to a value indicative to the relative presence of a given contaminant (such as a hematocrit value) in the liquid sample being measured.

For example, it is conceivable to use an appropriate amplifier for the purpose of amplifying a signal from the sensor (e.g. photodiode) indicative of the amount of light measured by the sensor, as well as circuitry for converting the amplified signal into a serial bit stream. For the purpose of calibrating the measurement apparatus, it is conceivable to provide "on-board" memory (e.g. lookup tables or the like). Components such as these would appear to be well-known to those of ordinary skill in the art and will thus not be further discussed herein. It is to be understood that components such as these are provided here only as an example, and that essentially any type of appropriate circuitry or other arrangement may be utilized within the scope of the present invention.

In view of the general considerations set forth hereinabove, the need to measure hematocrit levels of blood and blood products accurately, on-line (i.e. non-vasively) and in real time has been widely recognized, particularly with regards to the control of processes used to separate and/or treat the blood or blood fractions. The need to measure accurately what are considered very low hematocrit levels (i.e. less than about 10) has been deemed particularly important.

At least one embodiment of the present invention contemplates an apparatus and method in which preferably a single light source, such as one of narrowly defined wavelength with peak emission of about 466 nm (blue light), is used to emit light through a cuvette containing a blood or blood product sample to be measured. Further, a photodiode located on the other side of the sample cuvette detects the amount of light passing through the thin film sample. An amplifier and electronic circuit amplify the signal and convert the same into a serial bit stream. The amount of light detected by the photodiode is inversely proportional to the hematocrit level of the sample. As a result, it has been found that changes in hematocrit can be detected instantly. Preferably, calibration data will be stored in "on-board" memory.

In accordance with at least one embodiment of the present invention, it is contemplated that, in the context of a blood product sample containing a preponderance of white blood cells, hematocrit measurements can be taken prior to the sample being irradiated in an irradiation device. Such irradiation devices, and procedures associated therewith, are well-known to those of ordinary skill in the art.

Several U.S. Patents disclose apparatus and processes, as well as components and concepts associated therewith, that may be utilized in accordance with the embodiments of the present invention. These patents are listed herebelow and are incorporated by reference as if set forth in their entirety herein.

Some examples of irradiation devices, and procedures associated therewith, are to be found in the following U.S. Pat. Nos. 5,459,322 to Warkentin; Nos. 4,321,919, 4,398, 906 and 4,428,744 to Edelson; Nos. 4,708,715 and 4,692, 138 to Troutner et al.; No. 4,737,140 to Lee et al.; and Nos. 4,952,812 and 4,726,949 to Miropol et al.

U.S. Pat. Nos. 5,416,342 and 5,027,168 disclose examples of blue light-emitting diodes.

Blue light-emitting diodes are also discussed in "Technology Newsletter", *Electronic Design,* Oct. 24, 1995, page 29.

If not otherwise stated herein, it may be assumed that all components and/or processes described heretofore may, if appropriate, be considered to be interchangeable with similar components and/or processes disclosed elsewhere in the specification, unless an indication is made to the contrary.

It should be appreciated that the apparatus and method of the present invention may be configured and conducted as appropriate for the application. The embodiments described above are to be considered in all respects only as illustrative and not restrictive. The scope of the invention is defined by the following claims rather than by the foregoing description. All changes which come with the meaning and range of equivalency of the claims are to be embraced within their scope.

What is claimed is:

1. Device for measuring hematocrit, said device comprising:
   a light source for emitting light along a predetermined path;
   means for disposing a portion of a human blood sample in the path of light emitted by said light source wherein said light source emits light having a peak emission wavelength no greater than that of blue light;
   means for sensing light that has originated from said light source and that has passed through a portion of a human blood sample disposed, by said disposing means, in the path of light emitted by said light source; and
   means for converting the light sensed by said sensing means to a hematocrit value.

2. The device according to claim 1, wherein the light emitted by said light source has a peak emission wavelength of about 466 nm or less.

3. The device according to claim 1, wherein the light emitted by said light source has a peak emission wavelength substantially corresponding to that of blue light.

4. The device according to claim 3, wherein said light source emits light having a peak emission wavelength of about 466 nm.

5. The device according to claim 3, wherein said light source comprises a light-emitting diode.

6. The device according to claim 1, further comprising means for selectively accommodating said disposing means and for holding said disposing means substantially in the path of light emitted by said light source during the emission of light from said light source.

7. The device according to claim 6, wherein:
   said disposing means comprises a main portion, an infeed member and an outfeed member;
   said infeed and outfeed members respectively comprise conduits for receiving a human blood sample from a human blood sample source and for directing a human blood sample, having been disposed by said disposing means in the path of light emitted by said light source, to a human blood sample destination; and
   said main portion of said disposing means comprises means for receiving a human blood sample from said infeed portion and for disposing the human blood sample in a manner to optimize exposure of the human blood sample to the light originating from said light source.

8. The device according to claim 7, further comprising cover means for preventing the ingress of ambient light towards said main portion of said disposing means during the emission of light from said light-emitting diode.

9. A device for measuring hematocrit which comprises:
   a light source for emitting light along a predetermined path;
   means for disposing a portion of a human blood sample in the path of light emitted by said light source wherein said light source emits light having a peak emission wavelength no greater than that of blue light,
   means for sensing light that has originated from said light source and that has passed through a portion of a human blood sample disposed, by said disposing means, in the path of light emitted by said light source;
   means for converting the light sensed by said sensing means to a hematocrit value;
   means for selectively accommodating said disposing means and for holding said disposing means substantially in the path of light emitted by said light source during the emission of light from said light source;
   said disposing means comprising a main portion, an infeed member and an outfeed member;
   said infeed and outfeed members respectively comprising conduits for receiving a human blood sample from a human blood sample source and for directing a human blood sample, having been disposed by said disposing means in the path of light emitted by said light source, to a human blood sample destination;
   said main portion of said disposing means comprising means for receiving a human blood sample from said infeed portion and for disposing the human blood sample in a manner to optimize exposure of the human blood sample to the light originating from said light source;
   cover means for preventing the ingress of ambient light towards said main portion of said disposing means during the emission of light from said light-emitting diode; and
   wherein said means for selectively accommodating and holding said disposing means comprises a recessed portion configured to accommodate said main portion of said disposing means; and
   said main portion of said disposing means is dimensioned to be slideably accommodated within said recessed portion.

10. The device according to claim 9, wherein:
    said cover means comprises a cover being slideably mountable with respect to said recessed portion;
    said cover comprising a pair of recesses for respectively accommodating said infeed and outfeed members of said disposing means therewithin upon said main portion of said disposing means being slid into said recessed portion and said cover being slid into a covering position with respect to orienting means.

11. The device according to claim 10, wherein said main portion of said disposing means and said recessed portion are dimensioned and configured so as to orient a human blood sample in a plane that is substantially perpendicular to the path of light from said light source.

12. The device according to claim 11, further comprising:
    a first passage, extending from said light source to said recessed portion;
    a second passage, extending from said recessed portion to said sensing means; and
    said first and second passages being substantially aligned with one another and substantially coaxial with respect to one another.

13. The device according to claim 12, wherein said main portion of said disposing means and said recessed portion are configured such that a human blood sample being disposed by said disposing means is also in alignment with said first and second passages.

14. The device according to claim 13, wherein:
    said main portion comprises a testing chamber, said testing chamber comprising means for transforming a human blood sample having been received from said infeed member, into a substantially laminar layer and disposing a human blood sample substantially into a plane that is substantially perpendicular to the path of light emitted from said light source.

15. Apparatus for measuring a contaminant present in a liquid, said apparatus comprising:
    a light source for emitting light along a predetermined path;

means for temporarily disposing a portion of a liquid sample, said sample containing a contaminant portion and a non-contaminant portion, in the path of light emitted by said light source, the contaminant portion of the liquid being identifiable by emission thereof of light predominantly comprised of a first wavelength and the non-contaminant portion of the liquid being identifiable by emission thereof of light predominantly comprised of a second wavelength different from said first wavelength;

means for sensing light that has originated from said light source and that has passed through a portion of a liquid sample disposed, by said disposing means, in the path of light emitted by said light source; and means for converting the light sensed by said sensing means to a value indicative of the presence of the contaminant portion in the liquid sample;

wherein said light source comprises means for emitting light having a peak emission wavelength that is substantially no greater than said second wavelength.

16. The apparatus according to claim 15, wherein the light emitted by said light source substantially mimics UV-A light.

17. The apparatus according to claim 16, wherein the light emitted by said light source has a peak emission wavelength substantially no greater than that of blue light.

18. Method of measuring a contaminant present in a liquid, said method comprising the steps of:

providing a light source for emitting light along a predetermined path;

obtaining a liquid sample containing a contaminant portion and a non-contaminant portion, the contaminant portion of the liquid being identifiable thereof by emission of light predominantly comprised of a first wavelength and the non-contaminant portion of the liquid being identifiable by emission thereof of light predominantly comprised of a second wavelength different from the first wavelength, the non-contaminant portion having a given color;

disposing a portion of the liquid sample in the path of light emitted by the light source;

emitting light through the liquid sample portion;

sensing light that has originated from the light source and has passed through the liquid sample portion; and converting the light sensed to a value indicative of the relative presence of one of:
the contaminant portion in the liquid sample; and
the non-contaminant portion in the liquid sample;

wherein the light source emits light having a peak emission wavelength that is substantially no greater than the second wavelength.

19. The method according to claim 18, wherein the light sensed by the sensing means is converted to a value indicative of the relative presence of the contaminant portion in the liquid sample.

20. The method according to claim 18, wherein the emitted light substantially mimics UV-A light.

21. The method according to claim 20, wherein the emitted light has a peak emission wavelength substantially no greater than that of blue light.

22. The method according to claim 21, wherein the liquid sample is a portion of a human blood sample.

23. The method according to claim 22, wherein the liquid sample is a portion of a human blood sample containing predominantly white blood cells.

24. The method according to claim 23, being performed prior to the irradiation of the human blood sample in an ultraviolet irradiation apparatus.

25. The method according to claim 18, wherein the liquid sample is a portion of a human blood sample.

26. The method according to claim 25, wherein the liquid being disposed is a portion of a human blood sample containing predominantly white blood cells.

27. The method according to claim 26 being performed prior to the irradiation of the human blood sample in an ultraviolet irradiation apparatus.

* * * * *